United States Patent
Keibel

(10) Patent No.: US 8,504,188 B2
(45) Date of Patent: Aug. 6, 2013

(54) DEVICE AND METHOD FOR THE COMPUTER-ASSISTED GENERATION OF A MANIPULATOR PATH

(75) Inventor: Andreas Keibel, Augsburg (DE)

(73) Assignee: Kuka Laboratories GmbH, Augsburg (DE)

(*) Notice: Subject to any disclaimer, the term of this patent is extended or adjusted under 35 U.S.C. 154(b) by 146 days.

(21) Appl. No.: 12/997,016

(22) PCT Filed: May 14, 2009

(86) PCT No.: PCT/EP2009/003443
§ 371 (c)(1),
(2), (4) Date: Mar. 8, 2011

(87) PCT Pub. No.: WO2009/149805
PCT Pub. Date: Dec. 17, 2009

(65) Prior Publication Data
US 2011/0153297 A1   Jun. 23, 2011

(30) Foreign Application Priority Data
Jun. 9, 2008 (DE) .................. 10 2008 027 475

(51) Int. Cl.
*G06F 19/00* (2006.01)
*G05B 19/18* (2006.01)

(52) U.S. Cl.
USPC ........... 700/187; 700/184; 700/190; 700/193; 700/250; 700/262

(58) Field of Classification Search
USPC ............... 700/159–160, 173–175, 182–187, 700/192–194, 250–252, 262
See application file for complete search history.

(56) References Cited

U.S. PATENT DOCUMENTS

| | | | |
|---|---|---|---|
| 4,835,710 A * | 5/1989 | Schnelle et al. | 700/262 |
| 5,645,884 A | 7/1997 | Harlow, Jr. et al. | |
| 5,690,635 A * | 11/1997 | Matsen et al. | 606/88 |
| 7,466,099 B2 * | 12/2008 | McCoy, Jr. | 318/568.1 |
| 7,831,292 B2 * | 11/2010 | Quaid et al. | 600/424 |
| 2002/0082742 A1 * | 6/2002 | Kadono | 700/160 |
| 2003/0171842 A1 | 9/2003 | Teramoto et al. | |
| 2004/0015070 A1 * | 1/2004 | Liang et al. | 600/407 |
| 2004/0019407 A1 * | 1/2004 | Greene et al. | 700/245 |

(Continued)

FOREIGN PATENT DOCUMENTS

| | | |
|---|---|---|
| EP | 1 302 828 | 4/2003 |
| WO | WO 00/25285 | 5/2000 |
| WO | WO 2005/014241 | 2/2005 |

OTHER PUBLICATIONS

Local path modifications of heavy load manipulators; Dyllong et al., 2001 IEEE/ASME International Conference on Advanced Inteligent Mechatronics Preceedings, Jul. 8-12, 2001, pp. 464-469, 2001 IEEE.*

*Primary Examiner* — Ramesh Patel
(74) *Attorney, Agent, or Firm* — Schiff Hardin LLP

(57) ABSTRACT

In a method, device and in a non-transitory computer-readable storage medium for computer-assisted generation of a manipulator path of a computer-controlled manipulator, a processor is loaded with a virtual tool and generates a virtual tool path based in a virtual component and the loaded virtual tool. The processor is also loaded with a virtual manipulator kinematic and generates a virtual manipulator path based on the virtual tool path and the virtual manipulator kinematic.

11 Claims, 2 Drawing Sheets

U.S. PATENT DOCUMENTS

| | | |
|---|---|---|
| 2004/0213915 A1 | 10/2004 | Andersen |
| 2005/0128211 A1* | 6/2005 | Berger et al. ................. 345/582 |
| 2005/0166726 A1* | 8/2005 | Montesanti et al. ........... 82/1.11 |
| 2005/0246062 A1* | 11/2005 | Keibel .......................... 700/245 |
| 2006/0025890 A1 | 2/2006 | Nagatsuka et al. |
| 2007/0124107 A1* | 5/2007 | Numata et al. ................ 702/168 |
| 2010/0017185 A1* | 1/2010 | Bade et al. ...................... 703/13 |
| 2010/0317965 A1* | 12/2010 | Itkowitz et al. ............... 600/425 |

* cited by examiner

DEVICE AND METHOD FOR THE COMPUTER-ASSISTED GENERATION OF A MANIPULATOR PATH

BACKGROUND OF THE INVENTION

1. Field of the Invention

The present invention concerns a device and a method for computer-assisted generation of a manipulator path, and in particular for computer-assisted generation of a manipulator process.

2. Description of the Prior Art

A manipulator process generally includes a path for one or more manipulators, in particular robots and combinations of robots and additional axles such as linear axles, rotating or rotation-tilt tables, and an action order for one or more tools, in particular manipulator tools such as a gripper, a welding gun or the like. For example, a manipulator process for automatic mounting of a seal at motor vehicle door can include, among other things: the delivery of the door into a mounting cell via a first tool in the form of a conveyor belt or a first industrial robot, the positioning on a first axle of a rotating table, the application of an adhesive along an edge of the door via a second industrial robot with a second tool in the form of a glue gun, and the insertion of the door by a third industrial robot whose gripper represents a third tool. For this procedure, the second industrial robot moves along a manipulator path such that the glue gun that it directs follows edges of the door on a tool path and applies adhesive to different segments, i.e. the glue gun is activated and deactivated in a predetermined action sequence on the tool path.

A predetermined sequence of one or more positions is designated herein in general as a path, and a position defines the bearing and/or orientation. A tool path therefore includes one or more bearings and/or orientations of the tool, for example the bearing and orientation of a gripper, an exit opening of a glue gun or the like. A manipulator path correspondingly encompasses one or more poses of the manipulator—described for example in coordinate or articulation space by its joint positions or described in Cartesian work space (for example) by bearing and orientation of its TCPs ("Tool Center Points") that clearly arise from the joint positions—and, in the case of redundant manipulators or singular poses (possibly under consideration of additional boundary conditions), can be mapped to the joint positions via inverse transformation of the kinematics or, respectively, solving of the inverse kinematics.

In at least one position of a tool path, one or more process values of the tool can be altered in order to produce actions or, respectively, execute action sequences. For example, as process values the quantity of the output adhesive can be changed by varying the pressure given a glue gun; amperage and/or supplied welding wire volume can be changed given a welding gun; the opening angle or, respectively, opening times of the gripper tongs can be changed given a gripper; and so forth.

The process values of a manipulator-driven tool along a path of a manipulator, together with this path of the manipulator, thus describe a manipulator process in which a manipulator brings a tool into at least one position and there at least one process value of the tool is altered. Operation (for example in a finishing or mounting cell) of multiple manipulators or, respectively, tools together can form a manipulator process, as can the combination of the different manipulator paths and process value curves.

Such manipulator processes have conventionally been input step by step on site (for example in the mounting cell) into a manipulator controller via what is known as teaching, in which an operator with the manipulator adopts manual poses on the desired manipulator path that are subsequently connected into a manipulation path by a path generator of the manipulator controller. Problems—for example singular poses or poses that cannot be achieved, collisions and the like—are thereby only detected later, which requires time-consuming re-teaching. An optimization of the manipulator process by means of mathematical methods, like a transfer to other manipulators, is just barely possible.

In addition, offline programming is known. In this procedure, a control instruction whose execution by the manipulator controller directs the manipulator on the desired path is generated from a sequence of individual control commands that the operator inputs to a computer or the manipulator controller. However, due to the complex control commands that are respectively different for different manipulator controllers, this method requires highly qualified operators and is less intuitive, which in practice conflicts with a broad application. A modification of the manipulator process by changing the abstract control commands is complicated.

The early focus on the manipulator path in the planning of a manipulator process is common to both approaches, such that the manipulator that is used must already be established (known) at the beginning of the manipulator process planning and the manipulator path must thus be regenerated given a change of the manipulator that is used. The programming of manipulator paths via teaching or offline programming is for the most part only somewhat clear and prevents the wider use of manipulators, for example in artisan operations in which the user is primarily interested in the solution to the process task, for example the application of adhesive along a component edge.

SUMMARY OF THE INVENTION

An object of the present invention is to improve the generation of a manipulator path.

The present invention is based on the insight to orient on the process task to be solved in the generation of a manipulator path—for example the handling and/or processing of a work piece—and to generate the manipulator path dependent on this. While it has previously been sought to fulfill a process task with a preestablished manipulator, according to the invention the process task is now the focus, from which process task a manipulator path that is optimal for this and—in a preferred development—the complete manipulator process can be successively generated, which manipulator process also comprises (in addition to one or more manipulator paths) process value curves of one or more tools relative to the manipulator path or paths.

This procedure is more intuitive since an operator who is not versed in the handling of manipulators is primarily interested in the solution to the process task, thus for example wants to operate a tool in a specific manner and, according to the invention, is assisted in the generation of a manipulator path that is optimal for this. Additionally, the solution according to the invention leads to a more efficient manipulator path generation since in particular the agents required for this (in particular a manipulator path) are determined step by step deductively from the desired action, namely the solution to the process task. A computer-assisted method enables the partially automated realization of this principle.

A method according to the invention for computer-assisted generation of a manipulator process generates a virtual manipulator path that can be stored or, advantageously, a virtual manipulator process that can be stored, preferably in the form of an object-oriented process data model, and for this purpose implements the positioning of one or more virtual modules relative to a reference system by using a position device.

For example, the reference system can be a global coordinate system, a coordinate system of a mounting cell, a manipulator or the like. Positions—i.e. bearings and/or orientations of points, lines, surfaces, coordinates systems and the like—can be specified in this coordinate system. A user of a computer-assisted method can advantageously select a suitable reference system from a catalog. For example, different stored reference systems can map different cells with their boundary conditions, such as existing work spaces and shelters, obstacles and the like. If the computer-assisted generation takes place in an object-oriented manner in a particularly preferred embodiment, the reference system can be an object with corresponding properties.

One or more virtual components can be positioned relative to this reference system by means of the positioning device. Various properties can be associated with a virtual component, for example geometric dimensions, material data such as weight, elasticity, moment of inertia and the like. The virtual component can also preferably be selected from a library.

Virtual components with their properties are advantageously generated from numerical data (for instance production dimensions, CAD data, FEM data or the like) and imported into such a library or directly into the virtual manipulator process. In an object-oriented process data model they can be linked with the reference system in order to define their position relative to this. Virtual components can thereby be similarly at rest relative to the reference system (for instance if they map a mounting table in a mounting cell) or can move relative to the reference system (for instance if they map a tool on a transport belt). If multiple virtual components are present, their position can advantageously be defined relative to the reference system or another virtual component whose position relative to the reference system is defined directly or indirectly (i.e. via additional virtual components).

The positioning of the virtual components, just like additional method steps, particularly preferably ensues by means of a two-dimensional or three-dimensional editor (2D editor, 3D editor) that shows a two-dimensional or three-dimensional view of the reference system in which an operator can place or, respectively, edit objects with an input device, for instance a keyboard; a two-dimensional mouse; a trackball; a three-dimensional or multidimensional mouse (known as a "space mouse"); a joystick; a virtual reality input device such as a VR glove; or the like. The selection and positioning of a virtual component can then advantageously ensue by means of a drag-and-drop functionality.

To process a virtual component, the operator selects one or more virtual tools that are provided and loaded by a tool loading device according to the invention. These can also advantageously be selected from a library of stored, virtual tools that can be provided to the operator (for example by the manufacturer of the real tools) or generated by the operator by means of a suitable editor. A reference point of a manipulator, known as the TCP, can also form a virtual tool in order to generate pure transfer movements of a manipulator, for instance.

Specific properties can be associated with a virtual tool which can form an object in an object-oriented process data model. In addition to physical properties (for example mass and/or inertia of masses) in particular process values—for example the activation or, respectively, deactivation of a welding gun or glue gun, the opening and closing of a gripper, the application of a torque to a drilling or milling head or the like—can be associated with a virtual tool.

Additionally or alternatively, specific tool path conditions can also be associated with a virtual tool. For example, a glue gun is generally directed on an edge or in a movement pattern on a two-dimensional or three-dimensional surface in order to apply adhesive there. A drill is normally directed in a straight feed like. For example, the tool path condition that a tool path runs along an edge or on a surface can thus be associated with a virtual glue gun while the tool path condition that a tool path runs through a start point and end point of a bore or a touch-down point on a work piece, along a bore direction and up to a bore depth can be associated with a virtual drill.

In particular, degrees of freedom and/or constraints of a tool can be taken into account via such tool path conditions. A degree of freedom of a tool thereby in general describes an allowable position or position change, for example a displacement or rotation, while a constraint blocks a position or position change or allows it only depending on one or more degrees of freedom. For example, degrees of freedom and constraints can be defined relative to the virtual component that should be processed with the virtual tool or relative to Cartesian space.

For example, for specific adhesives and application types a glue gun should always be located above the adhesion point in order to prevent a contamination of the glue gun with adhesive dripping down from the application point, and given a start of a glue path said glue gun should be angled more significantly in the travel direction the faster that the glue gun moves relative to the component. The former can be realized via a constraint on a Cartesian basis that blocks an orientation of the glue gun with the exit facing upwards; the latter can be realized via a constraint on a component basis that predetermines an inclination angle of the glue gun depending on its travel velocity. Conversely, for example, a degree of freedom around its own rotation axis can be associated with a drill since a rotation of the tool around this axis has no significant effect on the process. Such degrees of freedom and constraints or other tool path conditions are advantageously automatically accounted for in the generation of the tool path by the tool path generation device.

The tool path generation device now generates a virtual tool path based on the virtual tool and the virtual component that is to be processed with said virtual tool. In a preferred embodiment, for this contour feature of the virtual component—for example vertices, edges, surfaces, curvature extremes or the like—to be processed are registered. The contour features to be registered thereby advantageously depend on the tool path conditions associated with the selected virtual tool. For example, if a glue gun is selected as a virtual tool, an associated tool path condition can be that the tool path runs along an edge (or edges) or on a surface or surfaces of the virtual component that are registered as contour features. If a vacuum gripper is selected as a virtual tool, an associated tool path condition can be that the gripper can cling to sufficiently large, flat surfaces, surfaces that can be manipulated well by this gripper are registered as contour features, for example. In the preferred embodiment of a 3D editor, a snap functionality can be provided for this purpose that—upon activation by the operator means of an input device—registers that contour (i.e. point, edge, surface or the like) that respectively lies closest to a visualization of the virtual tool.

In addition or as an alternative to the generation of the virtual tool path, tool positions can also be input independent of a component contour. For example, for cooling of a tool it can be advantageous to direct this between two contacts with a component into a position remote from said component.

For example, such tool positions can be input in a 3D editor by clicking on a three-dimensional, visualized position of the virtual tool relative to the reference system. Similar to the conventional teaching, in this way a TCP position can be approached, which improves the intuitive operability and simplifies the modification of automatically generated tool paths.

The virtual tool path is advantageously generated by means of a path generator on the basis of tool positions for the virtual tool that in particular can be input (as described in the preceding) by registering contour features and/or inputting tool positions independent of a component contour. For this a path generator is preferably used as it also underlies a manipulator controller. For example, a path generator can interpolate individual tool positions linearly, circularly, via splines or approximations in a known manner. One advantage of the use of a path generator that is also implemented in a manipulator controller is—in addition to its availability—that the real manipulator can very precisely realize a tool path generated in such a manner.

The tool path generated in such a manner is advantageously stored as an object of the object-oriented process data model that maps the virtual manipulator process.

If a virtual tool path is generated, the operator or a manipulator selection device selects a virtual manipulator kinematic that is provided and loaded according to the invention via a kinematics loading device. A manipulator kinematic describes the kinematics of a manipulator; for example, it can comprise the forward and/or backward transformation, in particular the mathematical description of the kinematic chain which maps the axial values of a manipulator at a position (i.e. bearing and/or orientation of a reference coordinate system, in particular of the TCP or a tool) (forward transformation or forward kinematics) or conversely yields the axis positions required to take up a predetermined tool position (backward transformation or backward kinematics). Accessibilities—i.e. a maximum possible work space of the manipulator, constrained positions (in particular singular poses and the like) can also arise from the manipulator kinematics. A manipulator selection device can thereby automatically choose a suitable virtual manipulator kinematics, for example based on predetermined boundary conditions and quality criteria (for instance the availability, the costs, the suitability or the like).

Since the manipulator kinematics result from the dimensions and joint positions, a virtual manipulator kinematic can be associated with every real manipulator. A virtual manipulator kinematic can thus in turn be selected from a library of possible manipulator kinematics (which, for example, is provided by a robot manufacturer) and linked with the virtual tool. This can be implemented by the user or program. For example, for this a reference coordinate system (in particular a TCP of the virtual manipulator kinematic) is positioned in a predetermined, advantageously constant position relative to the virtual tool, via which a synchronization between tool and manipulator is realized; a virtual manipulator "grips" the virtual tool, so to speak.

For the virtual manipulator kinematic a base position in the reference system can be determined that, for example, defines the position (i.e. bearing and/or orientation) of a stationary coordinate system of a manipulator base (known as the kinematic root) relative to the reference system. For this purpose, for example, the user can position a base coordinate system of the virtual manipulator kinematic in the reference system by means of the 3D editor, thus for example virtually place the manipulator in a mounting cell. Resulting from this is its pose or the axial positions that position the reference coordinate system of the virtual manipulator kinematic in the predetermined position relative to the virtual tool (for example the TCP of the virtual manipulator into congruence with a TOP of the virtual tool). However, the determination of the base position can also ensue in an automatic manner in that, for instance, the virtual manipulator kinematics are connected with average values for the respective joint or, respectively, axes are connected with a tool position of the virtual tool path, for instance a start, end or middle point. A virtual manipulator whose joints are located in a middle position is thus (so to speak) hanged on the virtual tool with its TCP, which virtual tool is located in the middle of the tool path; in this way a virtual manipulator can be initially positioned in a reference system such that it can realize the entire tool path with high probability. Hybrids are also possible in order to optimally place a redundant manipulator, for example.

Unsuitable manipulator kinematics or, respectively, base positions with which the planned tool path cannot be realized, for example, or with which the manipulator kinematic thereby assumes a disadvantageous pose (for instance a singular pose or a pose colliding with the component or the cell), can already be detected at this stage.

If the base position of the virtual manipulator kinematics and its linking with the virtual tool have been established, a virtual manipulator path on the basis of the virtual tool path and the virtual manipulator kinematics results, in particular by solving the reverse kinematic which maps the tool positions of the virtual tool path to poses of the virtual manipulator kinematic. Insofar as the virtual manipulator kinematic is redundant relative to the virtual tool path (thus exhibits more degrees of freedom than necessary to move the tool along the virtual tool path), suitable secondary conditions can be used to generate an optimal, unambiguous, virtual tool path in that (for instance) a distance from singular poses is maximized, deviations from middle joint positions are minimized or the like.

The manipulator path automatically generated in such a manner by a manipulator path generation device is advantageously likewise stored as an object of the object-oriented process data model that maps the virtual manipulator process.

According to a preferred embodiment of the present invention, process values are edited after the virtual tool path has been generated, thus similarly before or after the virtual manipulator path was generated. As was explained above, process values describe actions of a tool, thus for example the activation or, respectively, deactivation of a welding gun or glue gun, the opening or closing of a gripper, the application of a torque to a drilling or milling head or the like. If the path of a glue gun (for example) is thus generated, the user can predetermine the output of adhesive along this path; for instance, the user can increase the adhesive volume in specific path segments or traverse path segments without applying adhesive. For this a two-dimensional and/or three-dimensional process value editor is advantageously provided. For example, for this purpose a two-dimensional process value editor shows one or more process values (for instance the output adhesive volume, the torque of a drill or the like) as the ordinate over the time or the tool path coordinates as the abscissa. In this view the user can provide the action sequence of the tool in the manipulator process in a simple and intuitive manner by editing the curve (for example placing new or displacing existing process values by means of a mouse or another input device). A three-dimensional process editor shows one or more process values (for example the output adhesive volume) by means of (for example) points on the virtual tool path at which a process value changes, by means of color representation of the path depending on the process value and/or by means of a switchback representation of a process value over the virtual tool path or the like.

As used herein, an editing of process values encompass in equal measure the initialization or application and the modification or specification of specific, quantitative values of defined process values. For example, given a welding gun an operator can define whether the quantity of supplied welding wire is mapped as a process value, and then can predetermine this process value along the manipulator or tool path, for example predetermined specific, quantitative values per segment.

In a preferred embodiment of the present invention, the virtual tool path, the virtual manipulator path or the complete virtual manipulator process can be simulated, in particular can be graphically visualized or animated. The virtual tool path (including the modification of the process values) can thereby advantageously be simulated independent of the selected manipulator kinematics after the virtual tool path has been generated.

If a path generator as also forms the basis of a manipulator controller is used to generate the virtual tool path, the virtual manipulator path resulting from this advantageously already very precisely corresponds to the path that a real manipulator traverses upon realization of the manipulator process.

A further advantage lies in the faster reaction to changes to the virtual tool path or manipulator path: while in previous methods the complete manipulator program must first be generated by a programming environment depending on the manipulator type, passed to the manipulator controller and be processed by this, and the manipulator path or tool path is only generated from the results of the programming environment that result from this process, a virtual tool path or manipulator path that is generated with a path generator as also forms the basis of a manipulator controller can be scanned markedly faster. The reason for this is that the complete program code does not need to be generated and processed; rather, a path can be generated and displayed directly via the integrated path generator so that inputs of the operator that change the tool path or manipulator path (for example the additional input of tool positions) can be reacted to quickly, and the resulting, modified virtual tool path or manipulator path can be visualized. This again increases the intuitive operability.

The simulation enables a testing of the manipulator process generated according to the invention. In particular the arrival of kinematic conditions (for example kinematic constraints, unachievable poses or the like) can hereby be detected early in the planning. Additionally or alternatively, a visual or automatic collision testing can occur. In addition to such purely kinematic conditions, dynamic conditions can additionally or alternatively also be checked, for instance whether bearing load limits are complied with in all poses, drive or, respectively, braking powers are sufficient to realize the manipulator path and the like. A warning is advantageously output if kinematic or dynamic conditions are not satisfied. For example, for this purpose a corresponding region of the virtual tool path or manipulator path in which the virtual manipulator is located in or in proximity to a kinematic constraint, collision, bearing load overrun or the like can be colored or otherwise marked in the 3D editor.

A simulation of the entire manipulator process or of the manipulator path or, respectively, tool path advantageously also offers the possibility to optimize this/these by means of mathematical methods, for instance to determine an optimal velocity profile along the virtual tool path, to determine optimal tool positions or manipulator poses for component processing or the like.

With the method according to the invention that is explained in the preceding, a virtual manipulator process can be planned and possibly checked or optimized in a computer-assisted manner. In a particularly preferred embodiment of the present invention, such a manipulator process can also be realized simply and efficiently with one or more real manipulators.

For this purpose, in a preferred embodiment a control instruction for a manipulator is generated on the basis of the virtual manipulator process. Multiple real manipulators (for example industrial robots) and manipulator controllers (for example control cabinets) are frequently provided independent of one another. Therefore, various virtual manipulator controllers can in particular be provided that are provided to the operator in a library, for example, and are loaded from this. The reality of the different manipulators and manipulator controllers is simulated by the provision of different virtual manipulator kinematics and controllers, so to speak. A control instruction—i.e. a series of commands—is then automatically generated on the basis of the virtual manipulator controller selected by the operator and the virtual manipulator path or the virtual manipulator process to be realized, which control instruction realizes the virtual manipulator process, in particular the virtual manipulator path and action sequence of the tool. As in the platform-dependent conversion of a computer program from a high-level programming language into machine-readable code for different platforms, a control instruction for different manipulator controllers can thus be generated in a simple manner from the virtual manipulator process. The control instruction is subsequently transferred to a real manipulator controller.

The control instruction is consequently kept consistent in the real manipulator controller and the virtual manipulator process. For example, it can thus occur that an operator on site changes the control instruction of the manipulator, for instance manually re-teaches a robot path in a mounting cell. On the other hand, after the transfer of the control instruction to the manipulator controller changes to the planned manipulator process can result, for instance additional work tasks or a change to the process value curve.

Therefore, in a preferred embodiment of the present invention an equalization of the control instruction of the manipulator and that of the virtual manipulator process is implemented given changes to the control instruction or to the virtual manipulator process, for instance in that given a change to the virtual manipulator process a control instruction is generated again on the basis of the new virtual manipulator process and is transferred to the real manipulator controller. Conversely, a change to the control instruction in the real manipulator controller can be unambiguously mapped to the virtual manipulator process.

The realization of manipulator tasks is markedly facilitated in that the virtual manipulator process (advantageously in the form of an object-oriented process data model) is stored and is kept consistent with the control instruction in the real manipulator controller. For example, an operator with a portable computer on which a computer program to implement a method according to the invention is implemented and the virtual manipulator process is stored can thus implement a redesign of the manipulator process in a simple manner on site or transfer this to other manipulators. The editing capability of virtual manipulator processes that are stored and advantageously kept consistent with real control instructions, and thereby are further improved in practice, additionally allows the construction of a process library that facilitates the generation of new, similar manipulator processes on the basis of already stored, virtual manipulator processes. The storage as an object-oriented process data model enables a faster and more reliable testing and modification of the generated manipulator process.

Via the computer-assisted generation of a virtual manipulator process, this can advantageously be realized with various real manipulators and manipulator controllers. In a preferred embodiment of the present invention, the manipulator controller to which the control instruction is transferred is therefore selected from a plurality of available manipulator controllers. For example, if multiple free robots with the same kinematics and separate manipulator controllers are available in a real mounting cell, the control instruction is transferred to the manipulator controller of a selectable robot from this group. Selection and/or transfer preferably ensues over the network.

Due to the deviations between reality and virtual model, to realize a virtual manipulator process with a real manipulator it is advantageous to initially calibrate the real manipulator correspondingly. For this the operator takes up one or more calibration positions—for instance vertices of a work piece, mounting table or the like—with (for example) the tool of the manipulator. In the manipulator controller the control instruction is then calibrated on the basis of these calibration positions; a constant offset in individual joints is added or the like, for example, so that the real manipulator traverses the correct manipulator path relative to the work piece, mounting table or the like.

In a preferred embodiment of the present invention one or more virtual calibration positions are already defined for this upon generation of the virtual manipulator process. Preferred contour features of a virtual component can be registered for this. Information regarding the calibration positions is additionally stored; for example tables of the axle angles or two-dimensional or three-dimensional images of the calibration positions are generated and stored that, for instance, show a plan view of the points or surfaces to be traversed (occupied) for calibration from a selectable or fixed, predetermined perspective, for example from the point of view along a manipulator end element, from the point of view of a manipulator base or from the point of view of a selected position in the reference system.

The calibration positions are then transferred to the manipulator controller. During a calibration of the manipulator, this information—for example images on a display of the manipulator controller—is then displayed to the operator. In this way the operator intuitively knows which positions the operator should occupy for calibration and, with the manipulator, must only take up the position indicated in the images (advantageously marked via a coordinate system or the like) in order to calibrate said manipulator.

A device according to the invention for implementation of a method according to the present invention includes a positioning device, a tool loading device, a tool path generation device, a kinematic loading device and a manipulator path generation device, and a contour feature registration device, a tool position input device, a path generator, a path simulation and/or testing device, a process value editing device, a control instruction generation device, a memory device and/or additional devices to implement method steps described in the preceding. These examination volumes can be implemented, for example, together at a computer with an input device (for example keyboard, mouse, joystick or the like) and output device (for example monitor) or can also be distributed to various computers.

The invention also encompasses a non-transitory computer-readable storage medium that is programmed with programming instructions that, when the medium is loaded into a computerized processor that controls a manipulator system, cause the processor to implement the method steps described above, including all embodiments.

DESCRIPTION OF THE PREFERRED EMBODIMENTS

Figure 1:
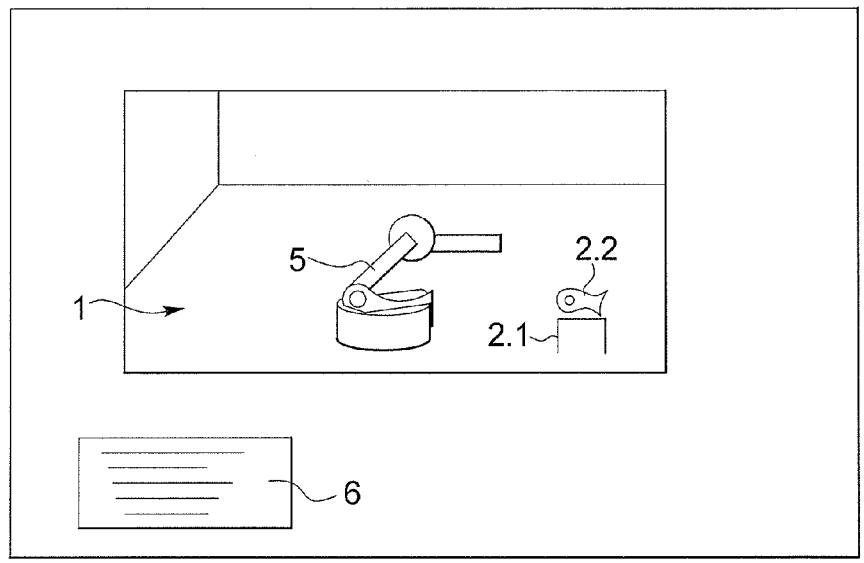
FIG. 1 schematically illustrates a 3D editor according to an embodiment of the present invention.
Figure 2:
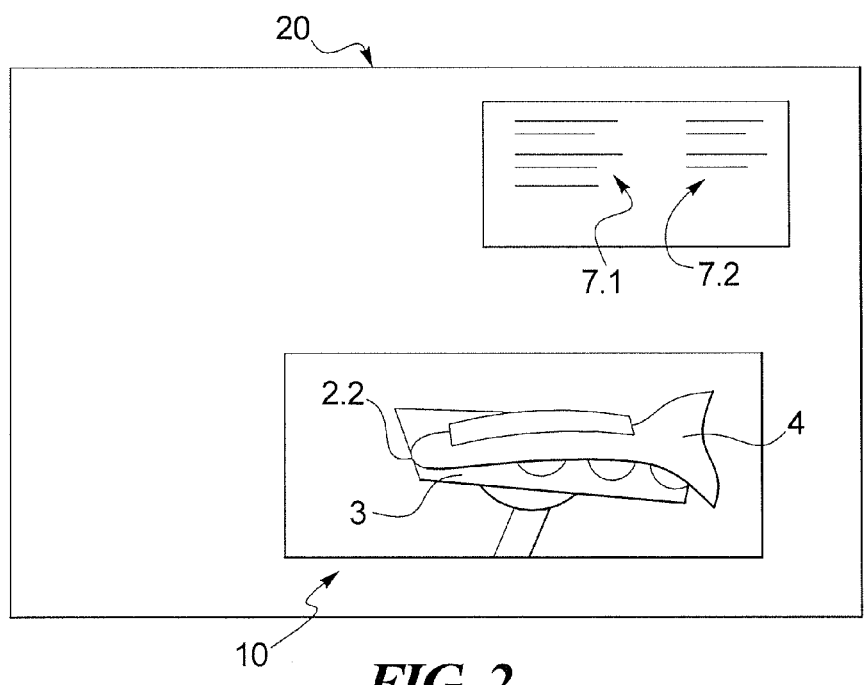
FIG. 2 schematically illustrates a 2D process editor according to an embodiment of the present invention, and the 3D editor according to FIG. 1.
Figure 3:
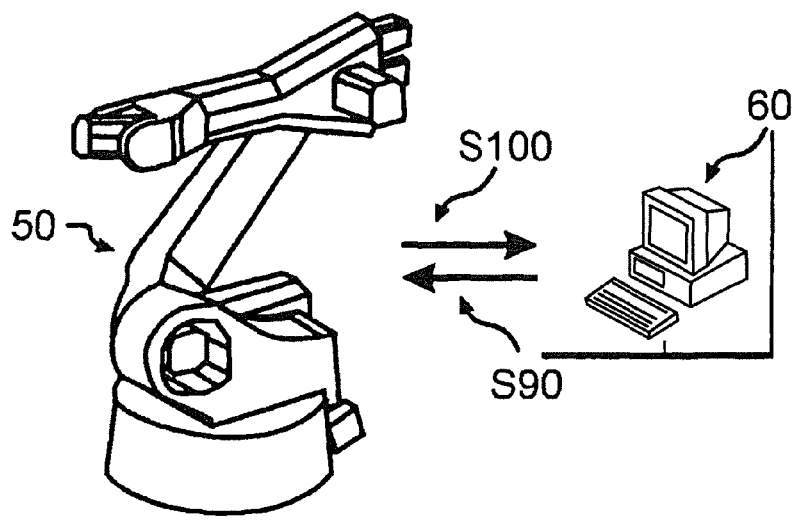
FIG. 3 schematically illustrates an industrial robot and a device according to an embodiment of the present invention.
Figure 4:
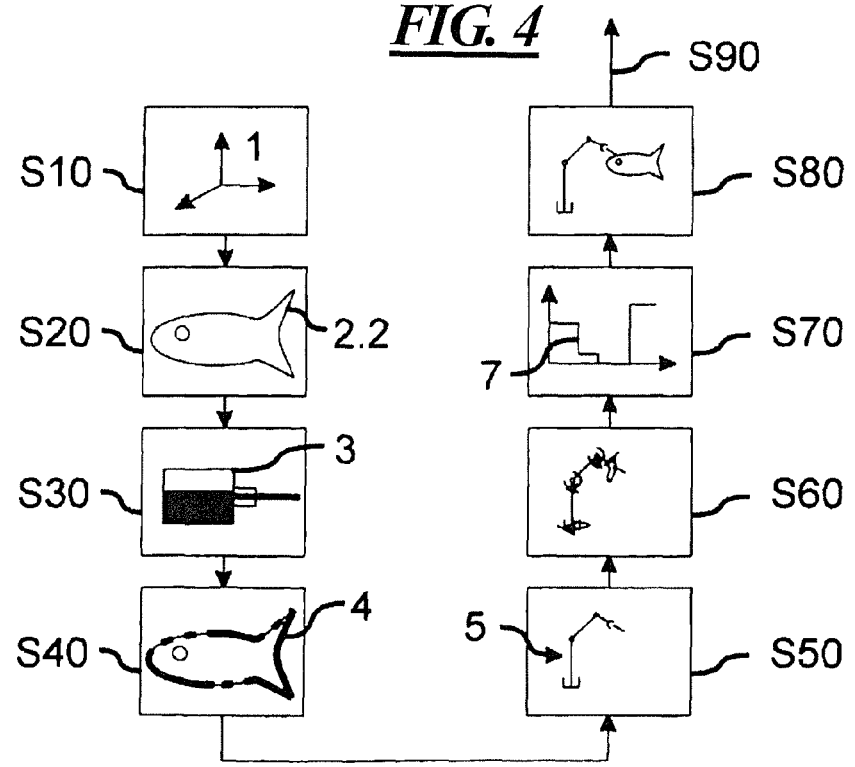
FIG. 4 is a flowchart of an embodiment of the method according to the present invention.

FIGS. 1 and 2 show views of a display of a 3D editor 10 or, respectively, 2D process value editor 20 with which a method according to one embodiment of the present invention (as represented schematically in FIG. 4) is executed on a computer 60 that is shown in FIG. 3 and that forms a device for computer-assisted generation of a manipulator process that is set up to implement the method according to FIG. 4 and that in particular possesses: a positioning device; a tool loading device; a tool path generation device; a kinematic loading device; and a manipulator path generation device (not shown).

For computer-assisted generation of a manipulator process by means of a method according to an embodiment of the present invention as is schematically shown in FIG. 4, a reference system 1 is initially selected from a library 6 (see FIG. 1)—for example a mounting cell or a global coordinate system—in Step S10. This is shown in the 3D editor 10 (see FIG. 1) and stored as an object of an object-oriented process model. In a preferred embodiment, a global coordinate system is thereby always provided as a reference system 1.

In Step S20 virtual components are subsequently positioned relative to the selected reference system 1. For this a mounting table 2.1 is selected from the library 6, for example, and positioned in the reference system 1 by a positioning device (for instance a mouse of the computer 60 in connection with corresponding software). An additional, virtual component in the form of a work piece 2.2 to be processed—which (for clarification) has a fish-like contour—is positioned on the mounting table 2.1 in the reference system 1. For this, objects that are correspondingly kinematically linked with the reference system object are inserted into the object-oriented process model. The virtual component 2.2 is thereby generated from CAD data of the work piece to be processed and is likewise provided in the library 6 from which it can then be loaded.

A virtual tool in the form of a glue gun 3 is now selected in Step S30 in that a corresponding object is loaded from the library 6 of the 3D editor 10 into the object-oriented process model.

In Step S40 a virtual tool path 4 is subsequently generated. After the search range has been specified, suitable contour features—for example edges, points, surfaces and/or polygons—on the virtual component 2.2 are registered by the computer 60 in the 3D editor 10 as an initial value for a virtual tool path 4. These can now be modified by tool positions on this path being removed or additional tool positions being added, and/or the orientations of the tool positions being adapted so that the virtual tool path 4 shown in FIG. 2 results. After possibly necessary node points of the virtual tool path 4 have been input, these are linked by means of a path interpolator (as it is also implemented in a robot controller) and thus the virtual tool path 4 is generated. Tool path conditions are taken into account, for example a constraint that blocks orientations of the glue gun 3 with the exit opening facing upward. The tool path can already be simulated (in particular graphically presented) at this point in time.

A virtual manipulator kinematic is selected in Step S50. For this virtual manipulator kinematics of usable, real manipulators—of the industrial robot 50 (FIG. 3), among others—are stored in the library 6. When the user selects one of these virtual manipulator kinematics, predetermines a position for its base coordinate system in the reference system 1 and connects the TCP of the virtual manipulator kinematics 5 with a reference coordinate system of the virtual tool 3, the user "places" the robot 50 in the mounting cell, which robot 50 virtually "grips" the glue gun 3. The virtual manipulator kinematic selected from the provided manipulator kinematics is loaded into the program and linked with the object-oriented process model for this.

Using the generated virtual tool path 4, in Step S60 the manipulator path generation device generates a virtual manipulator path in that joint angle curves for the individual axes of the virtual manipulator kinematic 5 are determined from the reverse transformation of the virtual manipulator kinematic.

In Step S70, process values 7 for the virtual tool 3 are now edited by means of the 2D process value editor 20. In the exemplary embodiment, values for adhesive pressure 7.1 and adhesive volume 7.2 are input for this along the tool path coordinates (abscissa).

In Step S80 the entire virtual manipulator process (thus the path 4 of the virtual glue gun 3, the path of the virtual manipulator 4 and the action sequence of the tool, i.e. the curve of the process values 7) is now simulated. In particular, kinematic conditions such as singular poses, constrained positions, accessibilities, collisions and dynamic conditions (in particular loading capacities and motor load limits) are thereby checked and the paths or process values curves are corrected as necessary. A mathematical optimization of the virtual manipulator process with regard to suitable quality criteria (for instance the process time) also additionally takes place.

In Step S80 a control instruction for a manipulator is subsequently generated on the basis of the virtual manipulator process in that the stored manipulator path is translated into corresponding control commands for a real manipulator controller. For this a corresponding virtual manipulator controller can be selected from the library 6 so that the same manipulator process can be realized with a plurality of different manipulators or manipulator controllers that respectively use different programming languages or, respectively, control commands. This control instruction is then transferred to a manipulator controller of a real robot 50 in Step S90.

During the execution of the manipulator process by this robot 50, a compensation of the control instruction of the manipulator and of the virtual manipulator process takes place given changes to the control instruction in the manipulator controller (for example by an operator on site who better adapts the process to real bounding conditions) or changes to the virtual manipulator process (for example to supplement additional process tasks such as the application of an additional glue seam). For this purpose, the computer 60 (on which the virtual manipulator process is stored as an object-oriented process data model that is correspondingly simple to modify) and the manipulator controller of the real robot 50 exchange data given modification of the virtual manipulator process or, respectively, of the control instruction in Step S100 or, respectively, S90.

If multiple manipulators or manipulator controllers are provided in a mounting cell that are respectively suitable for realization of the virtual manipulator process, an available manipulator or, respectively, an available manipulator controller is selected from this plurality before the transfer of the control instruction in Step S90.

Before starting up the robot 50, this should be calibrated so that it implements the planned manipulator process as exactly as possible. For this purpose, virtual calibration positions of the manipulator are generated in the 3D editor 10, for example distinctive vertices of the fish-shaped component 2.2. Images of the calibration positions are thereby generated that (for example in a three-dimensional view as shown in FIG. 1 or 2) show the respective selected calibration position—i.e. the position of the tool 3—which is based on the distinctive vertices of the fish-shaped component 2.2. These calibration positions and images are transferred to the manipulator controller of the robot 50.

During the calibration of the robot 50 by an operator on site, these images are then displayed so that the operator is provided with assistance as to which position he must next take up with the robot 50 in the calibration. The calibration time is hereby markedly shortened.

Although modifications and changes may be suggested by those skilled in the art, it is the intention of the inventor to embody within the patent warranted heron all changes and modifications as reasonably and properly come within the scope of his contribution to the art.

I claim as my invention:

1. A method for computer-assisted generation of a manipulator path, comprising:

providing and loading a virtual tool into a computerized processor, said virtual tool virtually mimicking an actual tool;

providing and loading a virtual component into said computerized processor, said virtual component virtually mimicking an actual component with which said actual tool is to interact in a tool/component interaction;

in said computerized processor, generating a virtual tool path of said virtual tool with respect to said virtual component in order to produce said tool/component interaction;

providing and loading a virtual manipulator kinematic into said computerized processor, said virtual manipulator kinematic virtually mimicking kinematics of an actual manipulator;

in said computerized processor, automatically generating a virtual manipulator path, to be implemented by said actual manipulator, based on said virtual tool path and said virtual manipulator kinematic, said virtual manipulator path comprising a part of a virtual manipulator process to be executed by said actual manipulator in order to produce said tool/component interaction, said virtual manipulator process having process values associated therewith;

providing and loading a virtual manipulator controller into said computerized processor, said virtual manipulator controller mimicking an actual controller that generates a control instruction for said actual manipulator based on said virtual manipulator controller and said virtual manipulator process;

via said computerized processor, allowing editing of said process values after said virtual tool path has been generated, and thereby producing an edited virtual manipulator process in said computerized processor, and allowing modification of said control instruction to produce a modified control instruction;

via said computerized processor, automatically conforming said control instruction or, when present, said modified control instruction, and the virtual manipulator process or, when present, the edited virtual manipulator process, to each other in order to produce at least one of an adapted control instruction and an adapted virtual manipulator process; and making the control instruction or, when present, the adapted control instruction, available at an output of said computerized processor in an electronic form transferrable to said actual manipulator controller for use by said actual manipulator controller to operate said actual manipulator.

2. Method according to claim 1, comprising at least one of:
registering contour features of the virtual component to generate the virtual tool path;
registering positions of the virtual tool by manual input to generate the virtual tool path;
using at least one of degrees of freedom constraints of the virtual tool are taken into account to generate the virtual tool path; and/or
generating the virtual tool and manipulator path using a path generator.

3. Method according to claim 1 comprising:
stimulating a least one of the virtual tool path and the virtual manipulator path at a display in communication with said processor.

4. Method according to claim 1 comprising:
implementing a test of at least one of the virtual tool path and the virtual manipulator path.

5. Method according to claim 4, comprising testing of the virtual manipulator path by at least one of:
testing kinematic conditions;
testing for collision; and
testing dynamic conditions.

6. Method according to claim 1, comprising:
selecting the manipulator controller to which the control instruction is transferred as an available manipulator controller from a plurality of manipulator controllers.

7. Method according to claim 1 comprising:
generating virtual calibration positions of the manipulator;
generating information comprising images of the calibration positions;
transferring the calibration positions to the manipulator controller; and
displaying the information during a calibration of the manipulator.

8. Method according to claim 1, comprising providing at least one of providing at least one of the virtual component, the virtual tool, the virtual manipulator kinematic and the virtual manipulator controller in a library and loading, said at least one of said virtual component, said virtual tool, said virtual manipulator kinematic and said virtual manipulator controller from said library.

9. Method according to claim 1 comprising:
electronically storing at least one of the virtual tool path, the virtual manipulator path and the virtual manipulator process.

10. A device for computer-assisted generation of a manipulator path, comprising:
a computerized processor;
an interface in communication with said computerized processor configured to receive load a virtual tool into the computerized processor, said virtual tool virtually mimicking an actual tool;
said interface being configured to receive and load a virtual component into said computerized processor, said virtual component virtually mimicking an actual component with which said actual tool is to interact in a tool/component interaction;
said computerized processor being configured to generate a virtual tool path of said virtual tool with respect to said virtual component in order to produce said tool/component interaction;
said interface being configured to receive and load a virtual manipulator kinematic into said computerized processor, said virtual manipulator kinematic virtually mimicking kinematics of an actual manipulator;
said computerized processor being configured to automatically generate a virtual manipulator path, to be implemented by said actual manipulator, based on said virtual tool path and said virtual manipulator kinematic, said virtual manipulator path comprising a part of a virtual manipulator process to be executed by said actual manipulator in order to produce said tool/component interaction, said virtual manipulator process having process values associated therewith;
said interface being configured to receive and load a virtual manipulator controller into said computerized processor, said virtual manipulator controller mimicking an actual controller that generates a control instruction for said actual manipulator based on said virtual manipulator controller and said virtual manipulator process;
said computerized processor being configured to allow editing of said process values after said virtual tool path has been generated, and thereby produce an edited virtual manipulator process in said computerized processor, and allow modification of said control instruction to produce a modified control instruction;
said computerized processor being configured to automatically conform said control instruction or, when present, said modified control instruction, and the virtual manipulator process or, when present, the edited virtual manipulator process, to each other in order to produce at least one of an adapted control instruction and an adapted virtual manipulator process; and
said computerized processor being configured to make the control parameter or, when present, the adapted control instruction available at an output of said computerized processor in an electronic form transferrable to said actual manipulator controller for use by said actual manipulator controller to operate said actual manipulator.

11. A non-transitory, computer-readable data storage medium encoded with programming instructions, said data storage medium being loaded into a computerized processor of a manipulator system, said programming instructions causing said computerized processor to:
load a virtual tool into a computerized processor, said virtual tool virtually mimicking an actual tool;
load a virtual component into said computerized processor, said virtual component virtually mimicking an actual component with which said actual tool is to interact in a tool/component interaction;
generate a virtual tool path of said virtual tool with respect to said virtual component in order to produce said tool/component interaction;

a virtual manipulator kinematic into said computerized processor, said virtual manipulator kinematic virtually mimicking kinematics of an actual manipulator;

automatically generate a virtual manipulator path, to be implemented by said actual manipulator, based on said virtual tool path and said virtual manipulator kinematic, said virtual manipulator path comprising a part of a virtual manipulator process to be executed by said actual manipulator in order to produce said tool/component interaction, said virtual manipulator process having process values associated therewith;

load a virtual manipulator controller into said computerized processor, said virtual manipulator controller mimicking an actual controller that generates a control instruction for said actual manipulator based on said virtual manipulator controller and said virtual manipulator process;

allow editing of said process values after said virtual tool path has been generated, and thereby produce an edited virtual manipulator process in said computerized processor, and allow modification of said control instruction to produce a modified control instruction;

conform said control instruction or, when present, said modified control instruction, and the virtual manipulator process or, when present, the edited virtual manipulator process to each other, in order to produce at least one of an adapted control instruction and an adapted virtual process; and make the control instruction or, when present, the adapted control instruction, available at an output of said computerized processor in an electronic form transferrable to said actual manipulator controller for use by said actual manipulator controller to operate said actual manipulator.

\* \* \* \* \*